United States Patent
Lim

(10) Patent No.: US 10,380,915 B2
(45) Date of Patent: Aug. 13, 2019

(54) BRAILLE DOT DELIVERY SYSTEM

(71) Applicant: Stephen Sophorn Lim, Desert Hot Springs, CA (US)

(72) Inventor: Stephen Sophorn Lim, Desert Hot Springs, CA (US)

( * ) Notice: Subject to any disclaimer, the term of this patent is extended or adjusted under 35 U.S.C. 154(b) by 167 days.

(21) Appl. No.: 15/638,025

(22) Filed: Jun. 29, 2017

(65) Prior Publication Data

US 2019/0005847 A1 Jan. 3, 2019

(51) Int. Cl.
*G09B 21/00* (2006.01)
*G06F 3/16* (2006.01)
*G09B 21/02* (2006.01)
*A61B 5/00* (2006.01)

(52) U.S. Cl.
CPC ............ *G09B 21/004* (2013.01); *G06F 3/16* (2013.01); *G09B 21/003* (2013.01); *G09B 21/025* (2013.01); *A61B 5/681* (2013.01); *G09B 21/02* (2013.01)

(58) Field of Classification Search
CPC .................................................. G09B 21/004
See application file for complete search history.

(56) References Cited

U.S. PATENT DOCUMENTS

| 5,580,251 | A | * | 12/1996 | Gilkes | G09B 21/003 340/407.1 |
| 2012/0295232 | A1 | * | 11/2012 | Lim | G09B 21/004 434/115 |
| 2014/0038139 | A1 | * | 2/2014 | AlDossary | G09B 21/001 434/114 |
| 2018/0217667 | A1 | * | 8/2018 | Park | G06F 3/014 |
| 2018/0275768 | A1 | * | 9/2018 | Karamafrooz | G06F 3/0202 |

FOREIGN PATENT DOCUMENTS

| JP | 2007095024 A | * | 4/2007 |
| KR | 20040040028 A | * | 5/2004 |
| KR | 101305235 B1 | * | 9/2013 |
| KR | 101360828 B1 | * | 2/2014 |
| KR | 101419003 B1 | * | 7/2014 |

* cited by examiner

*Primary Examiner* — Daniel J Colilla

(57) ABSTRACT

The Braille Dot Delivery System is an enhancement design from the Publication No.: US-2012-0295232-A1, which implements the same concept for delivering Braille Dot characters via electronic pulses; the system comprises of the Low Frequency Pulse Output Device Pad [140] and the Computer/Signal Transmitter [200], where the wireless receiving unit receives information from the Computer/Signal Transmitter [200] generates electrical pulse(s) to replicate a Braille dot-like character. The Low Frequency Pulse Output Device Pad [140] contain electrodes in a 3×2 matrix cell; each cell consists of a set of electrodes, one for positive signal and another negative signal or ground; completing the circuit is the electrode gel pad, a medium between the electrode cell insert and human skin surface contact, there delivers an electronic pulse at low applied current. The Computer/Signal Transmitter [200] allows for creating Braille Dot characters by the key buttons and functions as a central processing unit to communicate, transmit, and receives information with other devices like smart phone, tablet, laptop, desktop, World Wide Web, and other communication devices.

1 Claim, 4 Drawing Sheets

BRAILLE DOT DELIVERY SYSTEM

CROSS-REFERENCE TO RELATED APPLICATION application Ser. No. 13/135,979
File Date: Jul. 20, 2011
Publication No. US-2012-0295232-A1
Publication Date: Nov. 22, 2012

FEDERALLY SPONSORED RESEARCH

Not Applicable

SEQUENCE LISTING OR PROGRAM

Not Applicable

BACKGROUND OF THE INVENTION

Field of Invention

This development of the electronic Braille Dot Delivery System supersedes some of the designs of previous Publication No.: US-2012-0295232-A1, which implements the same electrical pulse concept for delivering the Braille dot language via method of the electrode cells. The Braille Dot Delivery System consists of two small devices, the Low Frequency Pulse Output Device Pad [140] and Computer/Signal transmitter [200], which are smaller, lighter in weight, and easy to implement devices for the visually impaired. The Low Frequency Pulse Output Device Pad [140] is a single 3×2 electrode cell matrix format designed to grip onto the palm, wrist or lower portion of the forearm of the human body; where the six electrode gels adhere flushed onto the human surface skin, while the Computer/Signal Transmitter [200] straps onto the forearm or about the area of the arm. The Computer/Signal Transmitter [200] allows for receiving information either from other computer, tablet, smart phones, World Wide Web, other compatible devices, communication devices, etc.; where as well, allows for input by the user with its special key arrangements and delivers information wirelessly to the Low Frequency Pulse Output Device Pad [140].

The concept from the previous publication of the Braille Touch Sense Device for delivering Braille Dot Language is in lieu of the mechanical components, in which method for obtaining the Braille Dot is through an electrical pulses that passes through to any of the six electrode cells; with enough current for the human skin to sense, the flushed surface contact between the human skin and electrodes can feel a slight protrusion by the electric current, like that of the Braille protruding dot(s). The instantaneous pulsation in the cell(s) represents a Braille dot character(s); the pulses can be programmed to deliver Braille words and sentences, through a scroll-like sequencing feature.

Description of Prior Invention

The Braille Touch Sense Display (TSD) of Publication No.: US-2012-0295232-A1, was a small portable computer that allows for the Braille characters to be typed and displayed via sensing method of an electronic pulse on its display surface, an all in one package. The generating of the electronic pulse concept eliminates the early mechanical rods and/or actuators/solenoids that resemble an embossed Braille dot. Other previous inventions prior to Publication No.: US-2012-0295232-A1, like that invented by Norman B. Sutherland with U.S. Pat. No. 3,659,354 and/or Robert C. Petersen of U.S. Pat. No. 4,871,992 contain many unique mechanical components. Mr. Sutherland implements pneumatics, air and vacuum to deliver the protrusion of the Braille dot, might be convenient at that time. Where as Mr. C. Peterson implements a spiral, rod, and pop-up method to allow protrusion of the Braille dot. Both are unique and creative at about their time, given that instruments and devices of that kind are essential to those of the visually impaired and that who requires similar apparatus for communication.

Objects and Advantages

In the previous publication no.: US-2012-0295232-A, the Braille Touch Sense Display (TSD) is a computer where the visually impaired can carry about their daily routine, input Braille dot and sense the Braille language. Contrary to the new developed Braille Dot Delivery System are two small devices, a wireless receiving peripheral and computer, which one device fits around the hypothenar area of the palm, lower forearm, or sections of the arm; as the electrode gels is placed flush to the skin of the palm area of the hand, delivers a low frequency electronic pulse, receives information from another device, which fits around the upper forearm, a computer and/or smart phone like device for keying, receiving and/or transmitting information. The approach with two small devices allows for both items to be strapped on the arm as the other arm can be function as for typing or inputting information into the system as illustrated in FIGS. 4 and 5 of this application.

SUMMARY OF THE INVENTION

This development invention introduces the Braille Dot Delivery System, an enhancement design from the Publication No.: US-2012-0295232-A1, the system consists of the Low Frequency Pulse Output Device Pad [140] and the Computer/Signal Transmitter [200] fits at the thenar region of the hand and the forearm region of the arm. The Low Frequency Pulse Output Device Pad [140] allows for low frequency electronic pulse, slightly enough currents for the human skin to sense, generates an electric pulse of a dot-like Braille character(s) to pass through the skin, as device is placed at the thenar region of the hand. The other Computer/Signal Transmitter [200] receives and delivers information via wireless technology to the Low Frequency Pulse Output Device Pad [140] and other communication devices like the smart phones, laptops, desktop, etc for World Wide Web communication.

With the same concept as the TSD of previous publication for electric pulse implementation to deliver Braille dot-like characters, the Low Frequency Pulse Output Device Pad [140] is slightly enhanced. At close observation at one of the cell matrix development contains two electrodes separated by an insulator inside a nominal round insert of the device pad, sits an electrode gel pad at about the device pad surface. One of the electrodes is allowed for positive current to pass through while the other electrode allow for negative or ground; the electric pulse system completes when current is applied and the gel pad is in contact with the human skin, there then current delivers a Braille dot-like character. The Computer/Signal Transmitter is a separate device designed to fit around the forearm of the hand using an of the market fastening system, there consists of unique key pads for delivering Braille dot character, and standard communication ports like USB, Micro-USB, Earphone, D/C adapter, Battery Slot, etc. for transmitting information to the Low Frequency Pulse Output Device Pad.

This Braille Dot Delivery System is not limited to just Braille communication applications but for many other forms of communications and applications. Some application ideas include communication of codes usage in different forms and/or method for delivering/receiving messages when creative observations are implemented. An example, if still used today, the Morse Codes can be implemented to deliver electronic pulse through touch beside visual and sound generation. Communication through touch sensing may be trade secrets that are useful to companies, corporations, government agencies, etc.

BRIEF DESCRIPTION OF THE DRAWINGS

Below is a brief description of the drawings, which also illustrates the components assemblies, applications, and views along with the reference number for the Braille Dot Delivery System.

DRAWINGS - Reference Numerals

Figure 1:
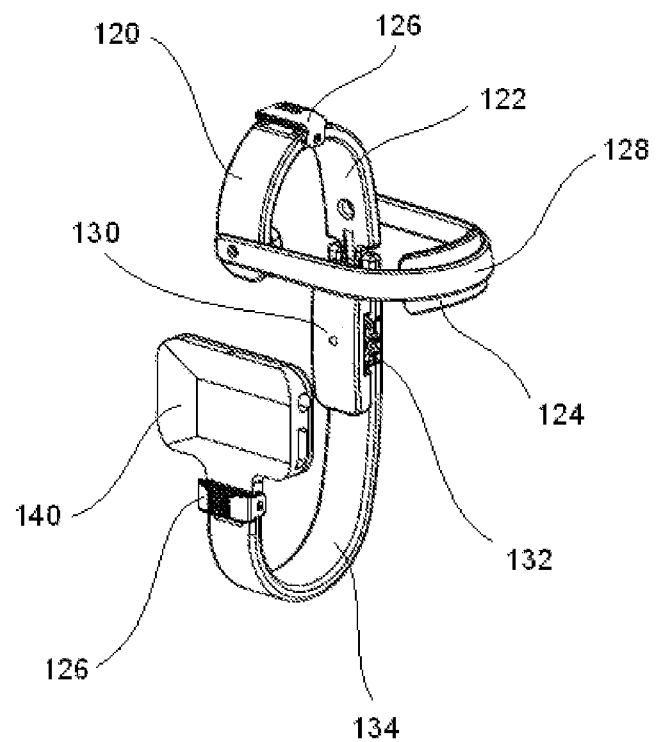
FIG. 1 illustrates a three-dimensional assembly view of the Braille Dot Delivery System wireless receiving unit that delivers the electrical pulse to replicate Braille Dot character along with the essential support straps for the hand.

| | | | |
|---|---|---|---|
| 10 | Position Electrode (A1) | 12 | Position Electrode (B1) |
| 14 | Position Electrode (A2) | 16 | Position Electrode (B2) |
| 18 | Position Electrode (A3) | 20 | Position Electrode (B3) |
| 22 | Negative Electrode (−) | 24 | Electrode Gel Pad |
| 26 | Electrode Gel Slot | | |
| 120 | Frontal Swing Frame | 122 | Upper Body Frame |
| 124 | Thenar Support Pad | 126 | Slider Button |
| 128 | Thenar Support Strap | 130 | Dorsum Cushion Pad |
| 132 | Adjustable Dorsum Knob | 134 | Lower Body Frame |
| 136 | Lock Pin | 138 | DC Power Supply Port |
| 140 | Low Frequency Pulse Output Device Pad | 142 | Headphone Port |
| 144 | Microphone Port | | |

DRAWINGS - Reference Numerals (continued)

| | | | |
|---|---|---|---|
| 200 | Computer/Signal Transmitter | 201 | Key Button (A1) |
| 202 | Key Button (A2) | 203 | Key Button (A3) |
| 204 | Key Button (B1) | 205 | Key Button (B2) |
| 206 | Key Button (B3) | 207 | Shift Button |
| 208 | Back Space Button | 209 | Enter Button |
| 210 | Micro USB Slot | 212 | Battery Pack Slot |

DETAILED DESCRIPTION OF THE INVENTION—FIG. 1—EMBODIMENT

A preferred embodiment in FIG. 1 derive a hand brace of the Braille dot delivery system, which components consist of the Frontal Swing Frame [120] attached to the Upper Body Frame [122] with an adjustable Slider Button [126], at the other end connects to a Lower Body Frame [134] with Lock Pins [136] allows for the Dorsum Cushion Pad [130] to center rest at the dorsum region of the back hand, along with an Adjustable Dorsum Knob [132] motions about normal to the dorsum region of the hand. The wireless receiving unit pad is the Low Frequency Pulse Output Device Pad [140], there attaches to one of the ends of the Lower Body Frame [134], adjustable and pivots implement through a Slider Button [126]. The Thenar Support Strap [128] with the Thenar Support Pad [124] ends are attached to the Upper Body Frame [122] and Frontal Swing Frame allows for quick fastening.

DETAILED DESCRIPTION—FIG. 1A—EMBODIMENT

Figure 1A:
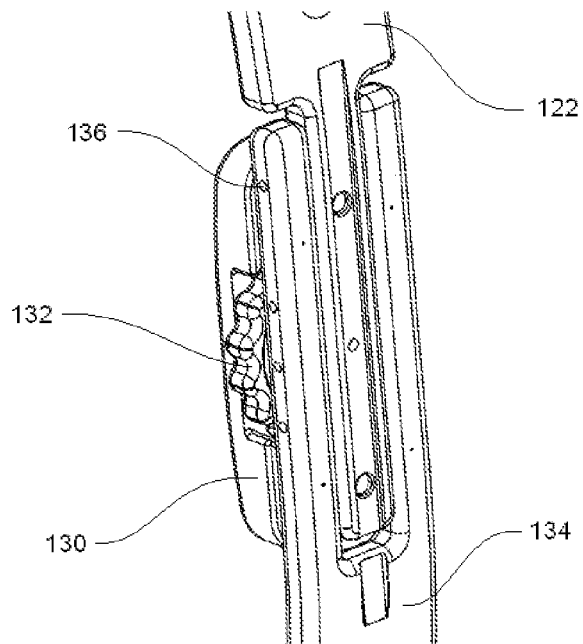
FIG. 1A illustrates a three-dimensional assembly view details the connection of the upper and lower body frame of the hand support strap with adjustable dorsum pad for adjustments to fit the dorsum area of the back of the hand.
Figure 2:
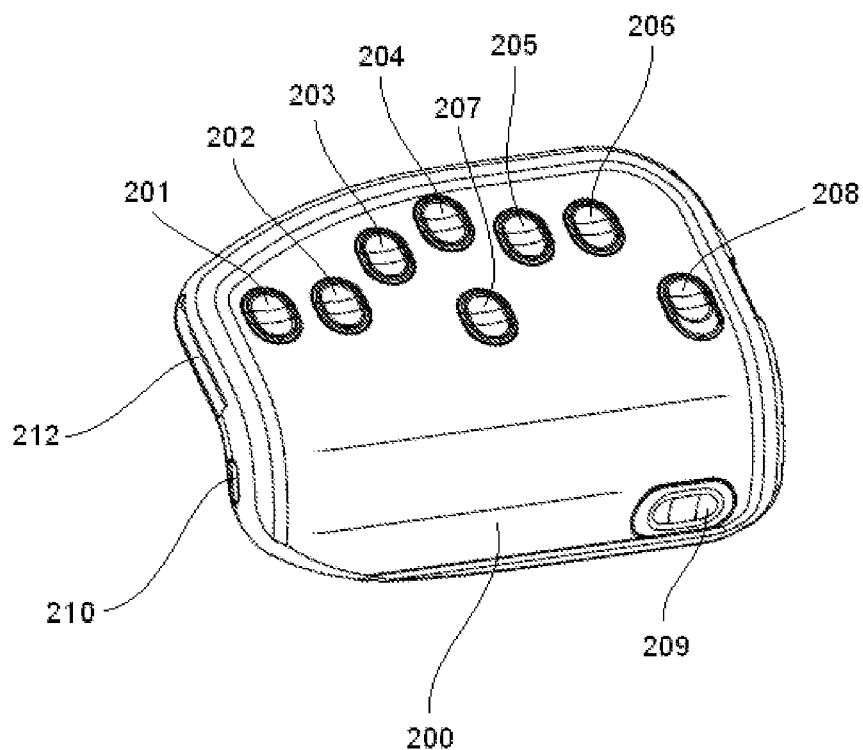
FIG. 2 illustrates the entire assembly of the main computer pad slightly curved design contains ergonomic input keys, slot, and communication port.
Figure 2A:
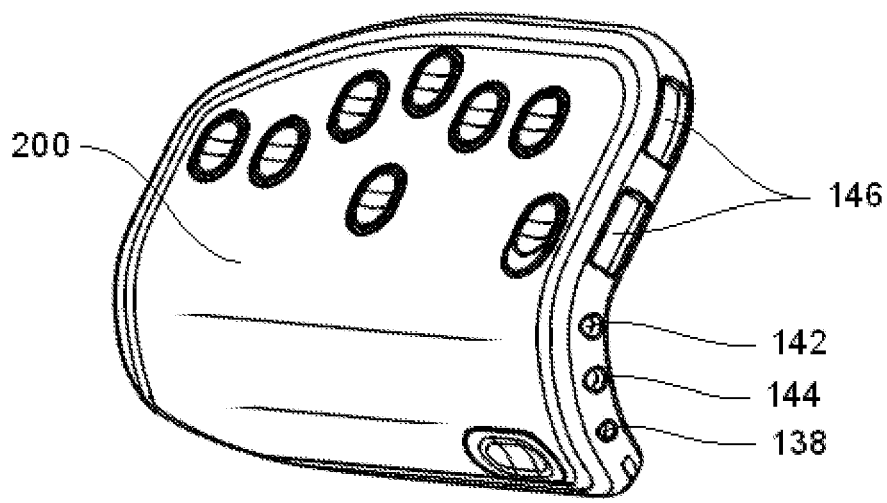
FIG. 2A illustrates the entire assembly of the other end of the main computer, which comprises of the standard communication ports, slots, and power charging port.

A preferred embodiment in FIG. 1A derives an assembly of the Upper Body Frame [122] and Lower Body Frame [134] where the Lock Pins [136] secure frame; the Dorsum Cushion Pad [130] place center normal to the body frame with rotating Adjustable Dorsum Knob [132].

DETAILED DESCRIPTION—FIGS. 2 AND 2A—EMBODIMENT

An embodiment of the Computer/Signal Transmitter [200] is slightly curved, comprises of input buttons, places the Position Keys [201], [202], [203], [204], [205], [206], Shift Key [207], Back Space Key [208] at normal to the larger surface of the computer; at smaller surface, positioned the Enter Button key [209] with unit Battery Slot [212], and a standard Micro-USB Slot [210] at the smaller side, allowing for standard USB ports [146], Headphone Port [142], Microphone Port [144], and DC power supply port [138] as standard communication ports placed at opposite end.

DETAILED DESCRIPTION—FIG. 3—EMBODIMENT

A preferred embodiment of the wireless receiving unit pad derives a Low Frequency Pulse Output Device Pad [140] contains a 3×2 matrix cell; within each cell slots are positive Position Electrode [10], [12], [14], [16], [18], [20] and Negative Electrode [22] separated by an insulator are the Negative Electrode [22]; normal to the surface of each cell slot of the Position Electrodes [10], [12], [14], [16], [18], [18] and Negative Electrode [22] are slots the Electrode Gel Slot [26].

DETAILED DESCRIPTION—FIG. 3A, AND 3B—EMBODIMENT

Figure 3:
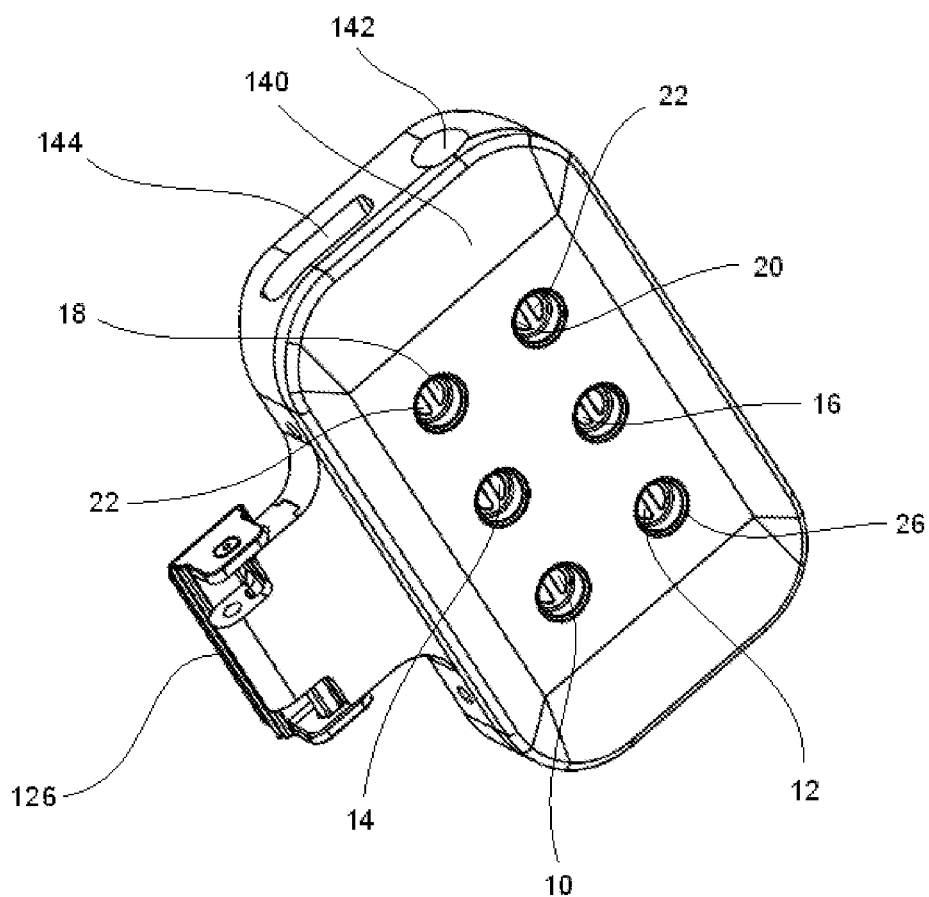
FIG. 3 is a detailed illustration of the wireless receiving unit pad for delivering low frequency electric pulse, contains a set of positive and negative electrodes paired inside each of the 3×2 cell matrix insert hole, for delivering Braille Dot character.
Figures 3A, 3B:
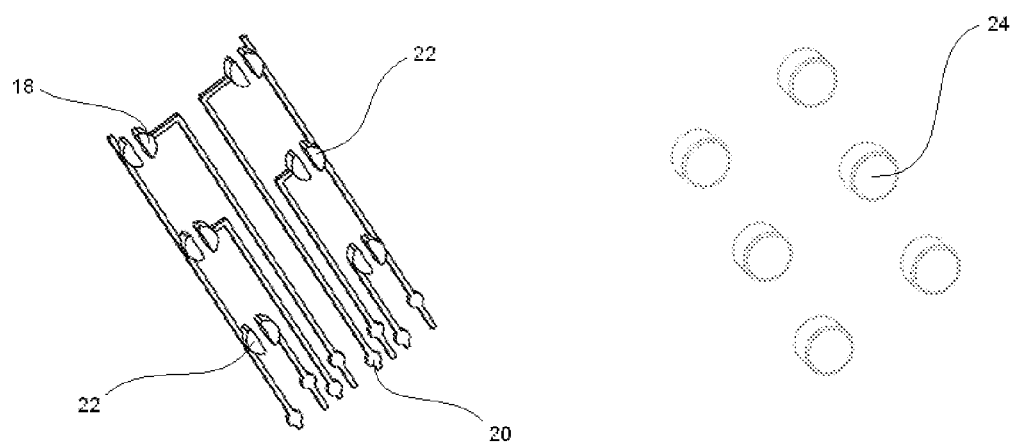
FIG. 3a are illustration of a set of positive and negative paired electrodes arranged in a 3×2 cell matrix for placement in a cell matrix insert.
FIG. 3b are close up of the electrode gel pads for contacts between the device pad and human skin surface, which skin surface can detect electric pulse as Braille Dot character.

An embodiment in FIG. 3a an 3B comprises of the paired electrodes arranged in a 3×2 cell matrix, where the Position Electrodes [10], [12], [14], [16], [18], [20] are placed towards the inner arrangement within the 3×2 cell matrix; where as, the Negative Electrodes [22] connected to ground positioned towards alongside the 3×2 cell matrix arrangement; with the Electrode Gel Pads [24] at nominal diameter and thickness to be placed within each of the 3×2 cell matrix inserts.

DETAILED DESCRIPTION—FIG. 4—EMBODIMENT

Figure 4:
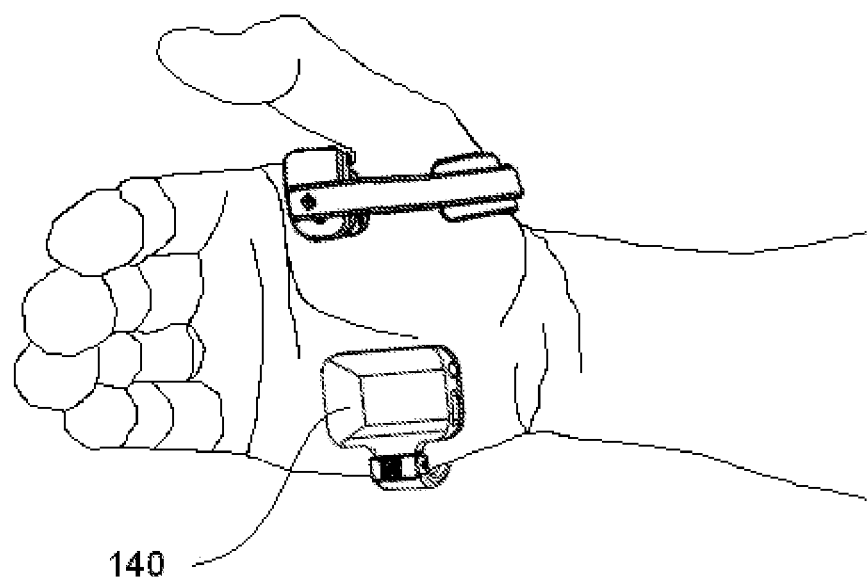
FIG. 4, is an application illustration of the wireless receiving unit pad placed at the hypothenar eminence area of the hand and support strap to the thenar eminence of the hand.

An embodiment of the Braille Dot Delivery System in FIG. 4 exhibits an application method, where the wireless receiving unit pad, the Low Frequency Pulse Output Device Pad [140] rest flushed on the hypothenar region of the palm, with support of the Thenar Support Strap and Pad rest along the thenar region of the hand.

DETAILED DESCRIPTION—FIG. 5—EMBODIMENT

Figure 5:
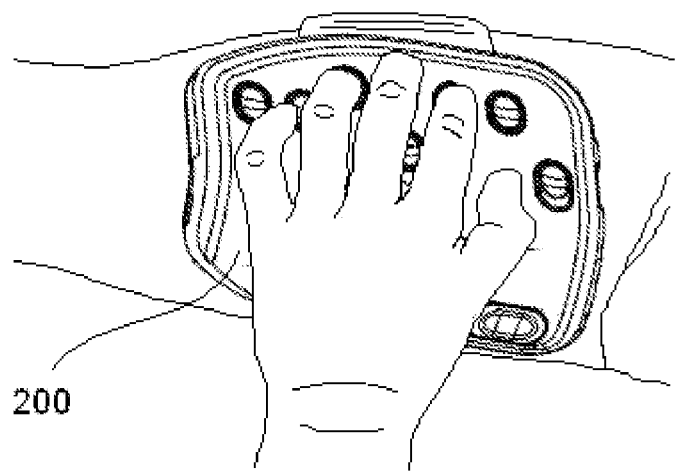
FIG. 5, is an application illustration of the slightly curved computer pad placed at the antebrachial of the arm.

An embodiment of the Braille Dot Delivery System in FIG. 5 exhibits an application method, where the Computer/Signal Transmitter [200] rest securely on the forearm of the arm demonstrates finger typing for inputting information and communication to the Low Frequency Pulse Output Device Pad [140].

Operations—FIGS. 3-3B, 4 and 5

The Braille Dot Delivery System comprised of the Low Frequency Pulse Output Device Pad [140] and the Computer/Signal Transmitter [200], was developed as a two separate unit for user ergonomically handling. The Low Frequency Pulse Output Device Pad [140] contains pair of electrodes positioned in a 3×2 matrix cell format, with each pair of positive and negative electrodes per for current passage, topped with an electrode Gel Pads [24] delivers just enough electric current to be felt by the human surface body. Calibration of the low level electric current delivery for sensing with human skin contact will varies from individuals to individuals.

When the Low Frequency Pulse Output Device Pad [140] is placed flushed at the hypothenar region of the palm, then secure strap with the body frame and dorsum pad, character development of a Braille Dot can deliver; observing the Low Frequency Pulse Output Device Pad [140], low level electric current or currents are required to pass through the positive Position Electrode [10], [12], [14], [16], [18], [20] and onto the Negative Electrode [22] as the Electrode Gel [24] adhering to the human skin surface provide a protruding dot effect.

The Low Frequency Pulse Output Device Pad [140] receives information wirelessly from the Computer/Signal Transmitter [200]. Depending on the number of Braille dot protrusion needed to develop Braille dot characters, each Position Electrodes may receive current signal simultaneously within the 3×2 matrix cells. To develop Braille Dot words, sentences, etc., program features within the Computer/Signal Transmitter [200] can be generated to sequencing electric current(s) or scroll-like signals features, then pass on to the Low Frequency Pulse Output Device Pad [140] wireless, there generates current to each matrix cell accordingly to deliver to human skin surface for Braille Dot characters.

As the main computation, the Computer/Signal Transmitter [200] receives two basic signals; one of the signals are from the ergonomics input Key Buttons [201], [202], [203], [204], [205], [206]; when pressed to developed a Braille Dot character words, signal is received for confirmation within the Computer/Signal Transmitter [200], then transmit via wireless communication to the Low Frequency Pulse Output Device Pad [140] to delivers Braille Dot character to the human skin surface for sensing. The second signal may be from other communication and peripheral devices such as smart phone, tablet, laptop, desktop, etc. and the World Wide Web. Additional features of the key buttons may be programmed for quick direct/access button. The Computer/Signal Transmitter [200] is design to fit onto the forearm region of the hand, is slightly curved with a strap to secure the device. There contains standard communication ports like that of a USB ports, Micro USB port, headphone, battery slot and DC power supply port.

The invention claimed is:

1. A Braille dot delivery system comprising:
a low frequency output device pad;
a frame;
frame straps, wherein the low frequency output device pad is configured to attach around a thenar region of a hand with the frame straps;
a central processing unit including a transmitter;
wherein the low frequency output device pad further comprises a 3×2 electrode cell matrix:
wherein each cell of the matrix comprises:
a cell slot with two electrodes separated by an insulator, wherein one electrode is positive (+) and one electrode is negative (−); and
a gel pad positioned in the cell slot;
wherein the low frequency pulse output device outputs a low electrical pulse capable of passing an electric current through human skin whereby a human can sense the electrical pulse.

* * * * *